United States Patent
Nakano et al.

(10) Patent No.: US 7,312,294 B2
(45) Date of Patent: Dec. 25, 2007

(54) NORBORNANE LACTONE (METH)ACRYLATE AND POLYMER THEREOF

(75) Inventors: Kenichi Nakano, Yokosuka (JP); Naoya Kutsuzawa, Yokosuka (JP); Toshikatsu Nojiri, Yokosuka (JP)

(73) Assignee: Toho Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/583,283

(22) PCT Filed: Dec. 17, 2004

(86) PCT No.: PCT/JP2004/018944

§ 371 (c)(1), (2), (4) Date: Jun. 16, 2006

(87) PCT Pub. No.: WO2005/058854

PCT Pub. Date: Jun. 30, 2005

(65) Prior Publication Data

US 2007/0117944 A1    May 24, 2007

(30) Foreign Application Priority Data

Dec. 18, 2003  (JP)  ............................. 2003-421704

(51) Int. Cl.
   *C08F 118/02*   (2006.01)
(52) U.S. Cl. ........................ 526/319; 524/556; 524/560
(58) Field of Classification Search ..................... None
   See application file for complete search history.

(56) References Cited

U.S. PATENT DOCUMENTS

2003/0077540 A1    4/2003  Kodama et al.
2003/0077543 A1*   4/2003  Sato ..................... 430/287.1
2006/0234154 A1*  10/2006  Nishimura et al. ...... 430/270.1

FOREIGN PATENT DOCUMENTS

| JP | A 7-140650 | 6/1995 |
| JP | A 2000-026446 | 1/2000 |
| JP | B2 3042618 | 3/2000 |
| JP | 2002351079 A * | 12/2002 |
| JP | A 2002-351079 | 12/2002 |
| JP | A 2003-270788 | 9/2003 |
| JP | A 2004-210917 | 7/2004 |
| JP | A 2004-220009 | 8/2004 |

OTHER PUBLICATIONS

Computer translation: Nishimura et al, "(Meth)acrylic polymer and radiation-sensitive resin composition", Jul. 29, 2004, JP-2004-210917.*

* cited by examiner

*Primary Examiner*—David W. Wu
*Assistant Examiner*—Karuna Reddy
(74) *Attorney, Agent, or Firm*—Oliff & Berridge PLC

(57) ABSTRACT

A norbornane lactone (meth)acrylate represented by the following general formula (1):

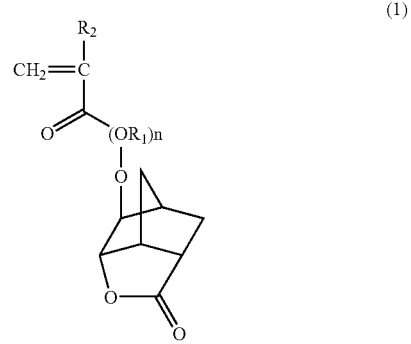

where $R_1$ denotes an alkylene group having 2 to 4 carbon atoms, n denotes an integer of 1 to 3, and $R_2$ denotes a hydrogen atom or methyl group.

5 Claims, No Drawings

NORBORNANE LACTONE (METH)ACRYLATE AND POLYMER THEREOF

TECHNICAL FIELD

The present invention relates to a new norbornane lactone (meth)acrylate and its (co)polymers, and in particular, to compounds whose use is expected as material of resist that can be preferably used for microfabrication using excimer laser, medicinal products, agricultural chemicals, and material of other precision chemical products. To be more specific, because norbornane lactone (meth)acrylate is liquid at ordinary temperature, it is easy to be handled, and since the (co)polymer provides outstanding dissolution characteristics to solvents, the present invention relates to compounds which are advantageous from the viewpoint of manufacturing process of semiconductors, etc.

BACKGROUND ART

In recent years, in the fields of semiconductors, liquid crystals, etc., miniaturization of devices by shortening the wavelength for the light source used in the lithography process has been rapidly taking place. Presently, the lithography technique using the KrF excimer laser (248 nm) for the light source has become the mainstream. To achieve further miniaturization, ArF excimer laser (193 nm) is about to be in use.

The structure of photoresist resin which can be suitably used is varied depending on the wavelength for the light source. In the event of using the KrF excimer laser light, polyhydroxy styrene with high transmissivity and derivatives thereof are popularly used. However, these have an aromatic ring that absorbs ultraviolet light at 200 nm or lower wavelength in its structure. Consequently, in the event that photoresist is formed by the use of the ArF excimer laser, the majority of exposure light is absorbed at the photoresist surface and the exposure light is difficult to transmit the resist inside, and consequently, it becomes difficult to accurately form the photoresist patterns.

In recent years, a large number of (meth)acrylates with alicyclic structure have been proposed as material of photoresists for higher density processing. Above all, ester compounds obtained by allowing 5-hydroxy-2,6-norbornane carbolactone to directly react with (meth)acrylic acid have no aromatic ring in their structures and in addition, polymers obtained by the use of the compounds provide superb dry-etching resistance, attracting keen attention of the people in various industries (Patent Literature 1).
Patent literature 1: Japanese Patent No. 3042618

DISCLOSURE OF INVENTION

Problem to Be Solved

However, because the ester compounds are solids at ordinary temperature, it is not easy to handle. Furthermore, (co)polymers which contain the ester compounds as components thereof provide low solubility to solvents, and are therefore disadvantageous in preparing high-concentration resist compositions. In particular, they have drawbacks of poor solubility in solvents such as propylene glycol monomethyl ether acetate, ethyl lactate, etc. which are suitably used for photoresist solvents.

It is the object of the present invention to provide a (meth)acrylate which is liquid at ordinary temperature and easy to handle, and it is another object of the present invention to provide a (meth)acrylate (co)polymer with improved solubility to solvents.

Means to Solve the Problem

The inventors devoted themselves to research in order to solve the problems and achieve the objects discussed above, and as a result, found that the structure of norbomane lactone (meth)acrylate exerts great effects on the solubility, and have completed the present invention. That is, the present invention relates to norbomane lactone (meth)acrylate represented by the following general formula (1).

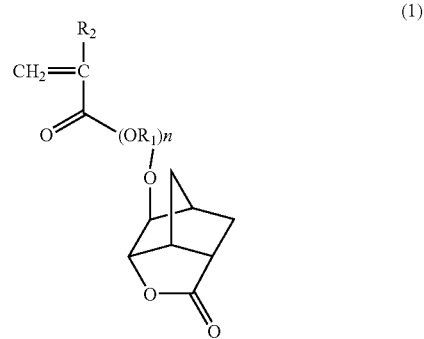

(wherein $R_1$ denotes an alkylene group having 2 to 4 carbon atoms, n denotes an integer of 1 to 3, and $R_2$ denotes a hydrogen atom or methyl group.)

The present invention is a (co)polymer obtained by polymerizing monomer mixture containing norbornane lactone (meth)acrylate represented by the general formula (1).

A preferable embodiment of the present invention relates to a (co)polymer which is obtained by polymerizing a monomer mixture containing at least one of compounds represented by the general formula (1) and at least one of compounds represented by the general formula (2):

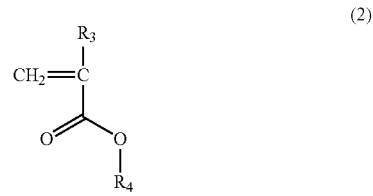

(wherein $R_3$ denotes a hydrogen atom or methyl group, $R_4$ denotes a substituted or unsubstituted hydrocarbon group having 3 to 19 carbon atoms) and whose weight-average molecular weight (Mw) is 2000 to 200000.

The present invention further relates to the above-mentioned (co)polymers, which are used as photoresist material.

EFFECT OF THE INVENTION

The norbornane lactone (meth)acrylate according to the present invention is liquid at room temperature, and furthermore, the (co)polymer obtained by polymerizing a monomer mixture containing the present compound provides good solubility to solvents, and more specifically, provides good solubility to propylene glycol monomethyl ether acetate and ethyl lactate. Consequently, the application as material for semiconductor photoresist resin, medicinal products, agricultural chemicals, and other precision chemical products is expected.

Best Mode For Carrying out the Invention

Now, the present invention will be described in detail as follows. In general formula (1), reference character $R_1$ denotes an alkylene group having 2 to 4 carbon atoms. Specific examples include ethylene group, propylene group, and butylene group. By addition reaction of alkylene oxide to 5-hydroxy-2,6-norbornane carbolactone, a (poly)oxyalkylene group expressed by $(R_1O)_n$ can be introduced. The addition reaction of alkylene oxide can be carried out by known methods using basic catalysts such as KOH, NaOH, etc. as required.

The "n" that indicates addition mol numbers of alkylene oxide in general formula (1) denotes an integer of 1 to 3, but is preferably an integer of 1 and 2 from the viewpoint of curability, and more preferably an integer of 1. When n exceeds 3, the density of the unsaturated group lowers and poor curability results. When n is 2 or more, $R_1$ may be same or different, and addition form of alkylene oxide may be random or block. In the event that the compound of the present invention is used as the material for photoresist for semiconductor manufacturing, high sensitivity is required; therefore, it is preferable that addition sol numbers of alkylene oxide is 1. In such event, by using butylene oxide as alkylene oxide, addition mol numbers can be easily brought to 1 mol. In addition, by using tertiary amine, in particular, triethylamine, as a catalyst for addition reactions, a 1-mol addition product can be comparatively easily obtained.

Norbornane lactone (meth)acrylate according to the present invention is a (meth)acrylated compound of alkylene oxide addition product (hereinafter called compound A) of 5-hydroxy-2,6-norbornane lactone obtained by the above-mentioned method. The compound can be obtained by allowing compound A to react with (meth)acrylic acid or chloride (meth)acrylate by known methods or by ester-exchanging with (meth)acrylic ester by known methods. Now, in the event that the reactive terminal of compound A is an oxybutylene group, the compound provides poor reactivity with (meth)acrylic acid, and it is therefore preferable to adopt the ester-exchange method.

In the general formula (2), specific examples of a substituted or unsubstituted hydrocarbon group having 3 to 19 carbon atoms which is represented by $R_4$ include t-butyl group, tetrahydropyran-2-yl group, tetrahydrofuran-2-yl group, 4-methoxy tetrahydropyran-4-yl group, 1-ethoxyethyl group, 1-butoxyethyl group, 1-propoxyethyl group, 3-oxocyclohexyl group, 2-methyl-2-adamantyl group, 8methyl-8-tricyclo[$5.2.1.0^{2,6}$]decyl group, or 1,2,7,7-tetramethyl-2-norbornyl group, 2-acetoxymenthyl group, 2-hydroxymenthyl group, 1-methyl-1-cyclohexylethyl group, tricylo[$5.2.1.0^{2,6}$]decylmethyl group having hydroxide group, carboxylic group, or ester group, tricycle[$5.2.1.0^{2,6}$]decyl group, adamantyl group, norbornyl group, methyl norbornyl group, isobornyl group, tetracyclo[$4.4.0.1^{2,5}.1^{7,10}$]dodecyl group, methyltetracyclo[$4.4.0.1^{2,5}.1^{7,10}$]dodecyl group, and others, but the present invention shall not be limited to these.

The weight-average molecular weight (Mw) of the (co) polymer according to the present invention is not particularly limited but is preferably between 2000 and 200000, and more preferably between 8000 and 25000.

Degree of dispersion (weight-average molecular weight (Mw) /number-average molecular weight (Mn)) of the (co) polymer of the present invention is not particularly limited but is preferably between 1.05 and 3.00, and more preferably between 1.10 and 2.50.

The copolymer according to the present invention is characterized by containing a component derived from norbornane lactone (meth)acrylate expressed by general formula (1), but in order to allow it to exhibit the expected effects in the present invention, the ratio is preferably 10 mol % or more, and more preferably 20 mol % or more, and in particular preferably 30 mol % or more. In addition, components derived from other copolymerizable monomers may be included to the extent that does not impair the effects obtained by the present invention.

The method for manufacturing the (co)polymer according to the present invention is not particularly limited, but it is convenient to dissolve the monomer and initiator in an organic solvent and to polymerize under known conditions. Alternatively, a method to dropwise add the monomer and initiator mixed in an organic solvent into an organic solvent kept to a certain temperature in advance and to polymerize for a specified time can be used.

The organic solvent used for polymerization is not particularly limited, but a solvent that can successfully dissolve a monomer and an obtained (co)polymer is preferable. Examples include 1,4-dioxane, acetone, methyl ethyl ketone, tetrahydrofuran, and others.

The initiator used for polymerization is not particularly limited, but examples include azo compounds such as azobisisobutylonitrile, 2,2'-azo-bis(2,4-dimetylvaleronitrile) and dimethyl 2,2'-azo-bis(2-methylpropionate), organic peroxides such as benzoyl peroxide, and furthermore, organic alkyl compounds such as n-butyllithium.

The polymerization temperature is not particularly limited, but is preferably between $-80°$ C. and $150°$ C., and more preferably between $-75°$ C. and $80°$ C. It is preferable to maintain the temperature for 5 to 10 hours after the desired temperature is reached and to carry out polymerization.

The refining method of the (co)polymer after completion of polymerization is not particularly limited, but a preferably refined (co)polymer can be obtained by appropriately diluting an obtained (co)polymer with a good solvent such as 1,4-dioxane, tetrahydrofuran, etc., and then dropwise adding the (co)polymer solution into a poor solvent such as water, hexane, etc. to be precipitated, filtered and dried. The (co)polymer obtained may be re-dissolved in a good solvent as required and the processes of dropwise addition in a poor solvent, filtration, and drying may be repeated.

By the foregoing process, the desired (co)polymer is obtained.

The obtained (co)polymer is prepared into a photoresist composition with the (co)polymer used as a base by compounding to this a suitable amount of a photoacid generator that generates acid by exposure to light.

By applying this chemically amplifying type photoresist composition on a semiconductor substrate (silicon wafer), exposing it to the light of 180 to 220-nm-wavelength using, for example, the ArF excimer laser, which is followed by baking, and then, developing, a super LSI, etc. with the desired patterns formed on the silicon wafer are manufactured.

EXAMPLE

Referring now to examples, the present invention will be described further more in detail, but the present invention shall not be limited to any of these examples. By the way, the properties, etc. in Examples and a Comparative Example were measured by the following methods.

(Weight-average Molecular Weight)

Twenty (20) mg of copolymer were dissolved in 5 mL of tetrahydrofuran and filtered by the 0.5-μm membrane filter to produce a sample solution, which was measured by gel permeation chromatography GPC-101 (manufactured by Shodex). For separation columns, Shodex GPC KF-G, KF-805, KF-803 and KF-802 (manufactured by Shodex) were used in series, tetrahydrofuran was used for the solvent, the flow rate was set to 1.0 mL/min, a differential refractometer was used for the detector, measuring temperature was set to 40° C., injection rate was set to 0.1 mL, and styrene was used as a standard polymer.

(Average Composition Ratio of the Copolymer)

The average composition ratio of the copolymer was found by measuring $^1$H-NMR. This measurement was carried out by the use of JNM-AL400 type FT-NMR (manufactured by Nihon Denshi Kabushiki Kaisha) with about 15 mass % bichloroform placed as the sample in a 5-mm-diameter tube, which was repeated at 64 times.

Example 1

In a 5L-autoclave, 770 g (5 mol) of 5-hydroxy-2,6-norbornane carbolactone (hereinafter referred to as "NLA"), 770 g of toluene, 10.1 g of triethylamine, and 432.7 g (6 mol) of butylene oxide were charged. After purging the autoclave with nitrogen, the autoclave was heated to 125° C. and the liquid was allowed to react for 8 hours at 125 to 130° C. The liquid composition after reaction was (unreacted NLA):(NLA-BO 1-mol adduct):(NLA-BO 2-mol adduct)=43:56:1 in the GC area ratio and the yield was 1,970 g. 300 g of the obtained reaction liquid were washed with 150 g of 10 wt % aqueous sodium hydroxide solution, and then, rinsed with water until the pH becomes neutral, and unreacted NLA was removed. After washing, solvent was removed to obtain a refined product of NLA-BO 1-mol adduct. GC purity: 93.8%; yield: 45.7 g; $^1$H-NMR(CDCl$_3$) δ0.95 (t, 3H); δ1.49 (m, 2H); δ1.58 (t, 3H); δ2.02 (m, 2H); δ2.33 (t, 1H); δ2.54 (m, 2H); δ3.16 (m, 1H); δ3.33 (m, 2H); δ3.51 (m, 1H); δ3.67 (m, 1H); and δ4.50(s, 1H). In addition, it was confirmed that the molecular weight is 226 by the CG-MS (CI method).

In a 300-mL flask with a water measuring tube, stirrer and thermometer, 30 g (0.13 mol) of NLA-BO 1-mol adduct obtained by the preceding synthesis, 131.7 g (1.31 mol) of methyl methacrylate, and 0.03 g of monomethoxy hydroquinone were charged. After rising temperature up to 100° C., 1.71 g (0.006 mol) of titanium tetraisopropoxide were added. While distillate was recovered, reactions were allowed to take place for 8 hours; then, unreacted methyl methacrylate was distilled, 100 g of water were added to deactivate catalysts, and deposits were removed by filtration. Then, the liquid was washed with 50 g of 10 wt % aqueous sodium hydroxide solution, and water rinsing was carried out further until pH became neutral. After washing, dewatering was carried out to obtain a pale orange clear liquid of NLA-BO 1-mol adduct methacrylate. GC purity: 95%; yield: 30 g; $^1$H-NMR (CDCl$_3$) δ0.93 (t, 3H); δ1.60 (m, 4H); δ1.95 (m, 5H); δ2.49 (m, 2H); δ3.12 (br, 1H); δ3.34 (s, 1H); δ3.55 (m, 2H); δ4.44 (m, 1H); δ4.97 (m, 1H); and δ5.57 (s, 1H) δ6.10 (s, 1H). In addition, it was confirmed that the molecular weight is 294 by the CG-MS (CI method).

Example 2

In a reactor vessel, 14.1 g of methacrylate obtained in Example 1, 25.1 g of 2-methyl-2-adamantyl methacrylate, 6.1 g of hydroxyl adamantyl methacrylate, 4.5 g of azo-bis-isobutylonitrile, and 110 g of dioxane were charged and polymerization reactions were carried out for 10 hours at 72° C. Then the reaction liquid was poured over 2000 g of hexane, and the deposits obtained were filter-separated. The deposits collected were dried under reduced pressure and dissolved in dioxane, and by repeating precipitation refining once again, 25 g of desired resin were obtained. The copolymerization ratio of this resin was (methacrylate obtained in Example 1):(2-methyl-2-adamantyl methacrylate):(hydroxyl adamantyl methacrylate)=35:50:15 from the integral ratio of $^1$H-NMR. The weight-average molecular weight (Mw) by GPC analysis was 14000 and the degree of dispersion (Mw/Mn) was 1.90.

Comparative Example 1

In a reactor vessel, 7.8 g of norbornane carbolactone methacrylate, 13.9 g of 2-methyl-2-adamantyl methacrylate, 3.4 g of hydroxyl adamantyl methacrylate, 3.3 g of azo-bis-isobutylonitrile, and 58 g of dioxane were charged and polymerization reaction was allowed to take place for 10 hours at 72° C. Then the reaction liquid was poured over 1,200 g of methanol, and the deposits generated were filter-separated. The deposits recovered were dried under reduced pressure and dissolved in dioxane, and precipitation refining was repeated once again to obtain 20 g of desired resin. The copolymerization ratio of this resin was (norbornane carbolactone methacrylate) (2-methyl-2-adamantyl methacrylate):(hydroxyl adamantyl methacrylate)=35:50:15 from the integral ratio of $^1$H-NMR. The weight-average molecular weight (Mw) by GPC analysis was 13000 and the degree of dispersion (Mw/Mn) was 1.90.

(Solubility Test)

0.5 g of resin and a specified quantity of a specific solvent were placed in a vial, and after agitating for 1 hour at 40° C., liquids free of insoluble matter and turbidity were judged dissolved.

◎: 30 wt % dissolved; ○: 20 wt % dissolved; X: insoluble (Results of Solubility Test)

Table 1 shows the results of tests on the solubility of resins obtained in Example 2 and Comparative Example 1 to various solvents.

TABLE 1

|  | EXAMPLE 2 | COMPARATIVE EXAMPLE 1 |
|---|---|---|
| Ethyl acetate | ◎ | X |
| PGMEA | ◎ | X |
| 2-heptanone | ◎ | X |
| Methyl ethyl ketone | ◎ | ◎ |
| Acetone | ◎ | ◎ |
| Dioxane | ◎ | ◎ |
| γ-butyrolactone | ◎ | ◎ |

TABLE 1-continued

| | EXAMPLE 2 | COMPARATIVE EXAMPLE 1 |
|---|---|---|
| ethyl lactate | ⊚ | ○ |
| PGME | ⊚ | X |

The foregoing results indicate that the polymer of the present invention provides better solubility as compared to Comparative Example. In particular, because the polymer of the present invention is freely soluble to propylene glycol monomethyl ether acetate and ethyl acetate, too, the polymer according to the present invention is suited for the photoresist material.

The invention claimed is:

1. A norbornane lactone (meth)acrylate represented by the following general formula (1):

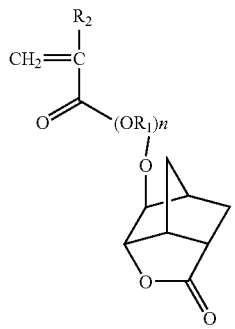
(1)

where $R_1$ denotes an alkylene group having 2 to 4 carbon atoms, n denotes an integer of 1 to 3, and $R_2$ denotes a hydrogen atom or methyl group.

2. copolymer obtained by polymerizing a monomer mixture containing norbornane lactone (meth)acrylate represented by the following general formula (1):

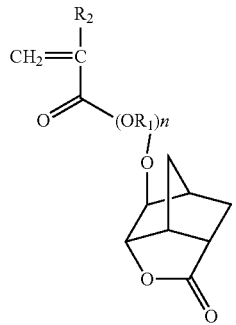
(1)

where $R_1$ denotes an alkylene group having 2 to 4 carbon atoms, n denotes an integer of 1 to 3, and $R_2$ denotes a hydrogen atom or methyl group.

3. The copolymer according to claim 2 which is obtained by polymerizing a monomer mixture containing at least one compound represented by general formula (1) and at least one of compounds expressed by the following general formula (2):

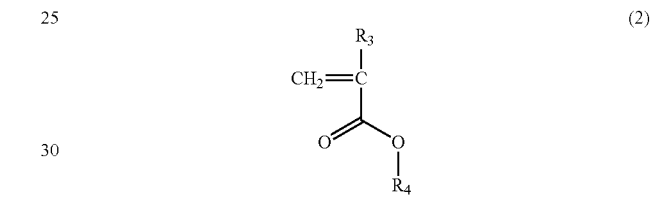
(2)

where $R_3$ denotes a hydrogen atom or methyl group, $R_4$ denotes a substituted or unsubstituted hydrocarbon group having 3 to 19 carbon atoms, and whose weight-average molecular weight (Mw) is 2000 to 200000.

4. A photoresist material comprising the copolymer according to claim 2.

5. A photoresist material comprising the copolymer according to claim 3.

* * * * *